(12) United States Patent
Rezgui et al.

(10) Patent No.: US 9,810,613 B2
(45) Date of Patent: Nov. 7, 2017

(54) SYSTEM AND METHOD FOR SENSING DISPLACEMENT OF SUBSEA STRUCTURES

(71) Applicant: Schlumberger Technology Corporation, Sugar Land, TX (US)

(72) Inventors: Fadhel Rezgui, Clamart (FR); Erik Rhein-Knudsen, Clamart (FR); Olivier Sindt, Sugar Land, TX (US); Vincent Alliot, Paris (FR); Patrice Ligneul, Elancourt (FR)

( * ) Notice: Subject to any disclaimer, the term of this patent is extended or adjusted under 35 U.S.C. 154(b) by 371 days.

(21) Appl. No.: 14/417,114

(22) PCT Filed: Jul. 24, 2013

(86) PCT No.: PCT/IB2013/056078
§ 371 (c)(1),
(2) Date: Jan. 23, 2015

(87) PCT Pub. No.: WO2014/016784
PCT Pub. Date: Jan. 30, 2014

(65) Prior Publication Data
US 2015/0211968 A1 Jul. 30, 2015

Related U.S. Application Data

(60) Provisional application No. 61/762,576, filed on Feb. 8, 2013, provisional application No. 61/729,983, filed (Continued)

(30) Foreign Application Priority Data

Jul. 24, 2012 (EP) ..................................... 12290250
Oct. 25, 2012 (EP) ..................................... 12189912

(51) Int. Cl.
*G01N 3/08* (2006.01)
*E21B 47/00* (2012.01)
(Continued)

(52) U.S. Cl.
CPC ............. *G01N 3/08* (2013.01); *E21B 17/012* (2013.01); *E21B 47/0006* (2013.01); *G01B 7/18* (2013.01);
(Continued)

(58) Field of Classification Search
CPC .... E21B 17/01; E21B 47/0006; E21B 17/012; Y10T 29/49895; G01M 5/0025;
(Continued)

(56) References Cited

U.S. PATENT DOCUMENTS 3,853,000 A 12/1974 Barnett et al.
4,505,018 A * 3/1985 Regalbuto ................. B25C 1/12
227/9

(Continued)

Primary Examiner — Harshad R Patel
Assistant Examiner — Brandi Hopkins
(74) Attorney, Agent, or Firm — Chamberlain Hrdlicka

(57) ABSTRACT

Systems and methods are described for monitoring displacement on structural elements of subsea systems such as on components of a subsea pipeline network used to transport production fluid from a subsurface wellhead to surface facilities. The described techniques sense changes in displacement using a sensing blade, for example made of crystalline material such as sapphire, that is anchored to the structural element such that it is approximately perpendicular to the direction of sensed displacement. Displacement is sensed as bending of the sensing blade using one or more instruments fabricated on the blade. Robustness of design is in part provided by additional flexible non-sensing blades mounted in parallel to the sensing blade.

31 Claims, 13 Drawing Sheets

Related U.S. Application Data on Nov. 26, 2012, provisional application No. 61/675,739, filed on Jul. 25, 2012.

(51) Int. Cl.

| | | |
|---|---|---|
| *G01M 5/00* | (2006.01) | |
| *G01B 7/16* | (2006.01) | |
| *G01L 1/22* | (2006.01) | |
| *G01L 5/10* | (2006.01) | |
| *E21B 17/01* | (2006.01) | |
| *G01D 5/02* | (2006.01) | |

(52) U.S. Cl.
CPC ............. *G01D 5/02* (2013.01); *G01L 1/2243* (2013.01); *G01L 5/102* (2013.01); *G01M 5/0025* (2013.01); *G01M 5/0083* (2013.01)

(58) Field of Classification Search
CPC ............. G01M 5/0091; G01M 5/0041; G01M 11/085; G01M 5/0083; G01N 3/08; G01D 5/02; G01L 1/2243; G01L 5/102; G01B 7/18
USPC .................. 73/800, 826, 816, 818, 760, 784; 405/188
See application file for complete search history.

(56) References Cited

U.S. PATENT DOCUMENTS

| | | | |
|---|---|---|---|
| 5,065,631 A * | 11/1991 | Ashpitel | G01B 5/30 73/786 |
| 5,099,700 A | 3/1992 | Morin et al. | |
| 2008/0303382 A1* | 12/2008 | Edwards, Jr. | G01L 5/102 310/328 |
| 2011/0259115 A1 | 10/2011 | Roberts et al. | |

* cited by examiner

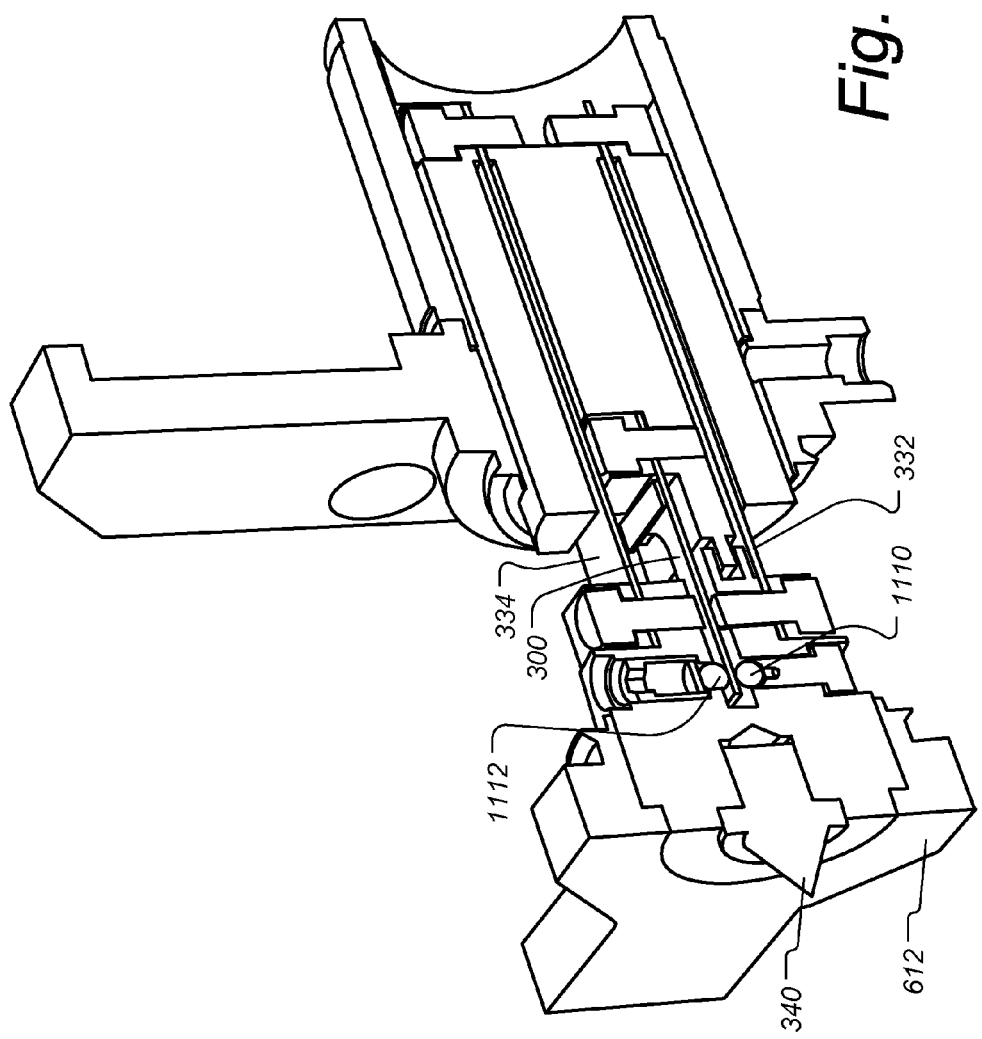

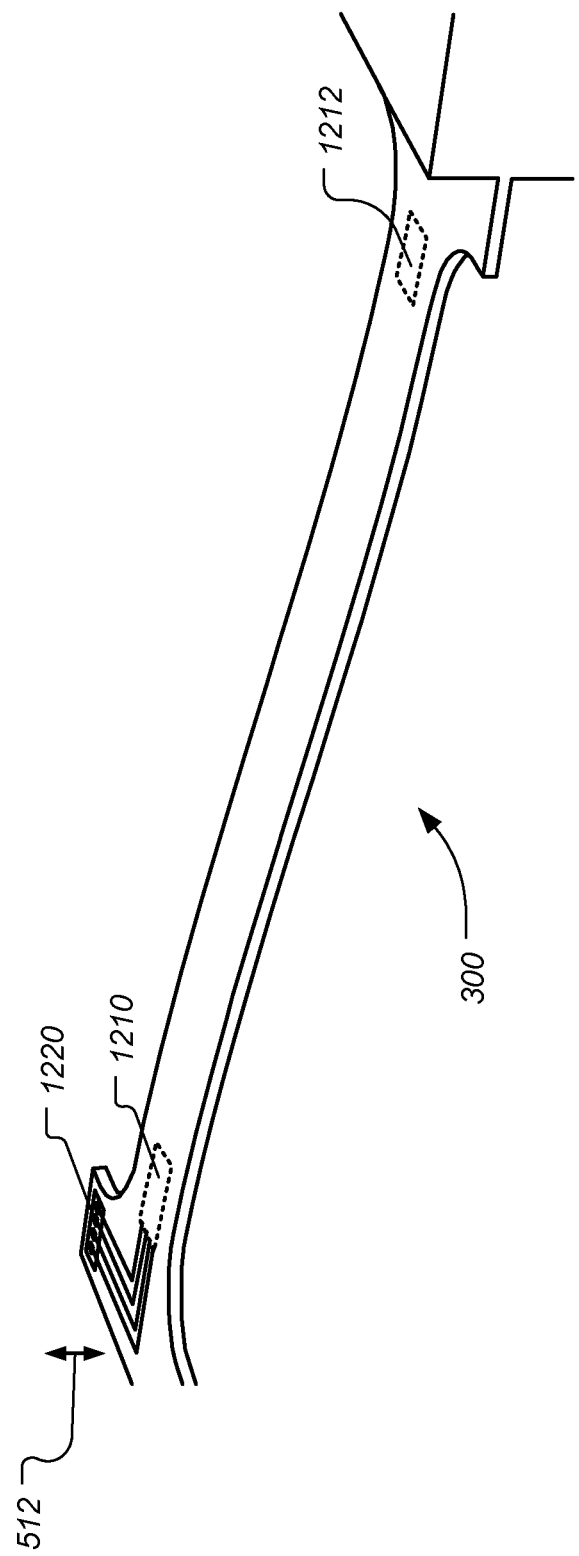

SYSTEM AND METHOD FOR SENSING DISPLACEMENT OF SUBSEA STRUCTURES

CROSS REFERENCE TO RELATED APPLICATIONS

This patent application claims the benefit of U.S. Prov. Ser. No. 61/675,739 filed Jul. 25, 2012; U.S. Prov. Ser. No. 61/729,983 filed Nov. 26, 2012; and U.S. Prov. Ser. No. 61/762,576 filed Feb. 8, 2013, each of which is incorporated by reference herein.

FIELD

This disclosure relates to methods and systems for displacement sensing and monitoring. More specifically, this disclosure relates to sensing and monitoring displacement on a structural component of subsea systems such a subsea pipeline networks to transport production fluid from a subsurface wellhead to surface facilities.

BACKGROUND

Pipe installations are subject to fatigue and potential damage which greatly benefit from permanently installed sensors for monitoring the status of these structures. Such monitoring aids in mitigating the risks associated with a possible loss of integrity. When monitoring such structures, it is often desirable to install the monitoring instrumentation intimately with the structures. One such monitoring objective is to measure the structural strain developed by the monitored system under a load.

Sensor technologies which could be used for such monitoring include: Linear Variable Differential Transformer (LVDT), Wheatstone bridges, and Fiber Optic with Bragg Grating. Generally, the strain sensors are mounted on a frame or on collars that constitute an interface between the structural element being monitored and the sensor itself. These interfaces allow for recovering and reinstalling the sensors onto the structural element for maintenance or repair. The sensor could also be directly bonded to the assets, which often makes it difficult or impossible to maintain or repair the sensor in case of sensor failure.

One example of such pipe installations relates to subsea applications wherein the structures are generally exposed to severe environmental conditions. Subsea hydrocarbon production systems using sea surface facilities of any sort require petroleum fluids to flow from the seabed to the surface through pipes called risers. The sea surface rises and falls with waves and tides, and the facilities are moved vertically, laterally and rotationally by various forces. The risers can either be steel pipes relying on their intrinsic flexibility or a range of flexible composite materials that are designed to resist the internal conveyance of fluids and the external forces imposed by all foreseen conditions. In another example, single line offset risers (SLHR) consist of a column of rigid pipe firmly attached to a foundation on the seabed and supported near the mean water level by a buoyancy can or tank. It is vital that these risers do not leak petroleum fluids to the environment, and do not suffer mechanical failures, which would require production to be stopped, causing severe loss of revenue. It might thus be beneficial to monitor integrity of such installations to mitigate risks associated with possible failure.

A typical field of application for subsea is a subsea oil and gas field architecture that integrates a pipeline network to transport the production fluid from the wellhead to the surface facilities. As part of this pipeline network the riser pipe structure is provided close to the surface process facilities to lift the fluid from the seabed to the surface. In deep and ultra deep water examples, operators have often adopted the hybrid free-standing riser concept which comprises: a seabed riser anchor base; a vertical single or bundled riser pipe(s) anchored to the seabed; a buoyancy tank providing an uplift tension to vertical riser pipe(s); a flexible pipe connecting the top of the vertical riser to the surface process facilities (FPSO); and a flexible joint connecting the buoyancy tank to the vertical riser. Accidental flooding of the buoyancy tank could create a potential hazard to the riser system and expose the field to catastrophic failure if a sufficient uplift tension is not applied to the vertical pipe system. In some applications, the buoyancy tank is made up of several independent compartments to limit the amount of water that could accidentally fill the tank. In order to further mitigate risks, subsea operators often request to install instrumentation to monitor possible accidental flooding of the buoyancy tank.

Generally, operators request that the tension generated by the buoyancy tank be monitored by means of an integrity monitoring system equipped with gages able to measure the pipe strain as shown. Such a system, well suited for detecting a sudden event, is more limited in the case of a slow water intrusion inside the tank, for example, due to corrosion. Readings collected from the tension collar may drift and the instrument cannot be recalibrated subsea. As a result, it is difficult to differentiate real water ingress from the data drift. Further, in some cases it is desirable to provide a secondary and independent monitoring system for redundancy and increased security.

SUMMARY

According to some embodiments a method is described for sensing displacement on a subsea structural system. The method includes sensing displacement between a first location on structural element of the subsea structural system and a second location on the structural element, the sensing being based at least in part on a sensing element having a crystalline material substrate. According to some embodiments the crystalline material is sapphire or quartz, and one or more sensor instruments are formed on the substrate so as to detect bending of the sensing element.

According to some embodiments, the subsea structural system is a subsea riser system configured to lift a production fluid from a subsurface wellhead to a surface facility. In some examples, the subsea riser system includes an uplift system, such as buoyancy tank, configured to provide uplift tension on components of the subsea riser system, and the structural element is under tension due to the uplift tension and the sensing of displacement is used to monitor the integrity of the uplift system. According to some embodiments, the sensed displacement is used to determine one or more other properties associated with the structural element such as: force; tension; strain or torque.

According to some embodiments, an alert signal is automatically transmitted to a surface facility when a predetermined threshold value relating to the structural element is met. According to some embodiments the sensing system including the sensing element can be installed on the structural element using an ROV unit.

According to some embodiments, a system for sensing displacement on a subsea structural system is described. The displacement sensing system includes: an elongated frame having a first end and a second end; a first anchoring system mounted to the first end of the frame and configured to fixedly anchor the displacement sensing system to a structural element of the subsea structural system at a first location; a second anchoring system configured to fixedly anchor the displacement sensing system to the structural element at a second location; and a sensing element having a crystalline material substrate with a major longitudinal axis, first and second ends, and at least one sensor instrument formed on the crystalline material substrate configured to sense bending of the sensing element substrate. The sensing element is mounted and configured such that displacement between the first and second locations can be sensed as bending of the sensing element. According to some embodiments the sensor instruments are two independent strain bridge resistors formed on the crystalline material substrate, which can be configured to operate in opposite modes. According to some embodiments, the first and second anchoring systems comprise one or more spikes configured to penetrate the structural element upon installation of the displacement sensing system on the structural element. One or more flexible non-sensing blades can be mounted in parallel with the sensing element to increase physical robustness.

According to some embodiments, a method is described for sensing displacement on a subsea structural system. The method includes: sensing bending of an elongated sensing element having a major longitudinal axis and at least one sensor instrument configured to sense bending of the sensing element; and sensing displacement in a sensed displacement direction between first and second locations on a structural element of the subsea structural system. The displacement sensing is based on the sensed bending of the elongated sensing element. The sensing element is configured and mounted such that the major longitudinal axis is non-parallel to the sensed displacement direction, and such that displacement between the first and second locations is directly transmitted to bending of the sensing element. According to some embodiments, the major longitudinal axis of the sensing element is approximately perpendicular to the sensed displacement direction. According to some embodiments the sensing element is made of a crystalline substrate, and according to some other embodiments the sensing element is made of a polycrystalline material such as a metal or of an amorphous material.

According to some embodiments, a system is described for sensing displacement on a subsea structural system. The displacement sensing system includes: an elongated frame having a first end and a second end; a first anchoring system mounted to the first end of the frame and configured to fixedly anchor the displacement sensing system to a structural element of the subsea structural system at a first location; a second anchoring system configured to fixedly anchor the displacement sensing system to the structural element at a second location; and a sensing element having a major longitudinal axis, first and second ends, and at least one sensor instrument formed thereon configured to sense bending of the sensing element. The sensing element is mounted and configured such that displacement along a sensed displacement direction between the first and second locations can be sensed as bending of the sensing element and such that the major longitudinal axis is non-parallel to the sensed displacement direction. According to some embodiments, the major longitudinal axis of the sensing element is perpendicular, or approximately perpendicular to the sensed displacement direction. According some embodiments, the first end of the sensing element is fixed in rigid relationship with the second end of the frame, and the second end of the sensing element is fixed in rigid relationship with the second anchoring system. According to some other embodiments, one end of the sensing element is fixed and the other end is movably attached, such as by contacting rounded bearing surfaces.

BRIEF DESCRIPTION OF THE DRAWINGS

The subject disclosure is further described in the detailed description which follows, in reference to the noted plurality of drawings by way of non-limiting examples of embodiments of the subject disclosure, in which like reference numerals represent similar parts throughout the several views of the drawings, and wherein:

FIGS. 9-1 and 9-2 are diagrams illustrating physical principal aspects of a displacement sensing system, according to some embodiments;

FIG. 11 is a cross section perspective view of aspects of a displacement sensing system using a semi-attached sensing blade, according to some embodiments; and FIG. 12 is a perspective view illustrating aspects of a sapphire blade for use in displacement sensing, according to some embodiments.

DETAILED DESCRIPTION

The particulars shown herein are by way of example, and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details of the subject disclosure in more detail than is necessary for the fundamental understanding of the subject disclosure, the description taken with the drawings making apparent to those skilled in the art how the several forms of the subject disclosure may be embodied in practice. Further, like reference numbers and designations in the various drawings indicate like elements.

According to some embodiments, a sensor apparatus and method for displacement measurement are described. The measurement is made by bending an instrumented blade equipped with one or several sensing means. The system includes an anchor means that can lock the sensor extremity to the structure being monitored so that any structural deformation or deflexion is directly transmitted to the sensor by bending the instrumented blade. Depending on the interface frame between the sensor with the structural element being monitored, this system can be configured to measure pulling force, torque, bending moments, strain, elongation, internal pipe pressure, and/or any load deformation experienced by a structure. This measurement apparatus can be either ab initio installed for continuous or discrete monitoring and/or can be retrofitted to existing facilities.

Figure 1:
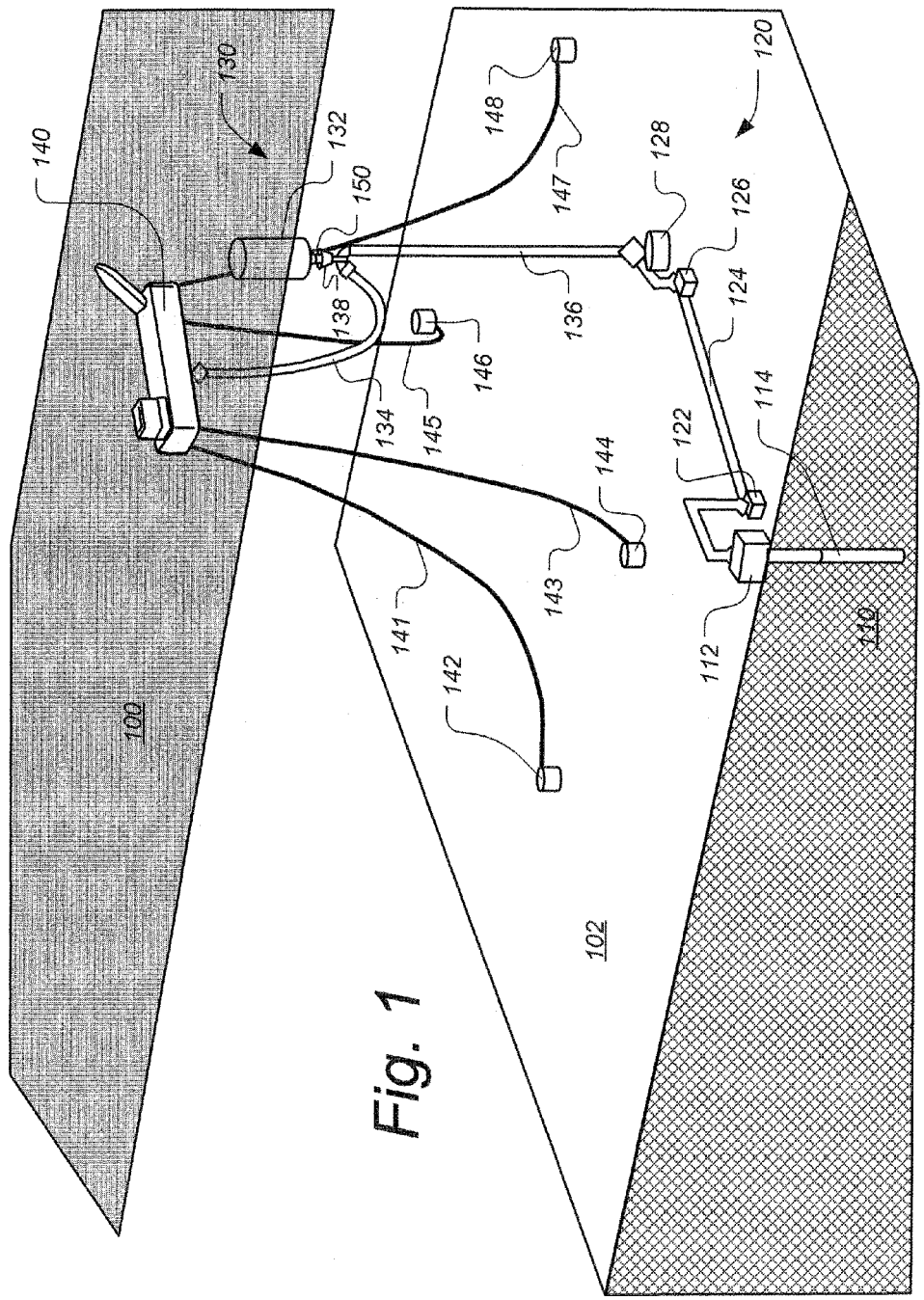
FIG. 1 illustrates a subsea oil and gas field architecture in which some embodiments are used.

FIG. 1 illustrates a subsea oil and gas field architecture in which some embodiments are used. The subsea and gas field architecture shown integrates a pipeline network 120 to transport production fluid from the wellhead 112 on the seafloor 102 to the surface facilities on the sea surface 100. Wellhead 112 draws production fluid from subterranean rock formation 110 via wellbore 114. In the example shown in FIG. 1, the production fluid flows along sea floor flowline 124 that is terminated by pipe termination 122 one end and by spool piece 126 on the other end. As part of pipeline network 120 a riser pipe structure 130 is provided close to the surface process facilities to lift the fluid from the seabed 102 to the sea surface 100. In some examples of this network 120, for deep and ultra-deep water, operators have adopted a hybrid free-standing riser architecture which comprises: seabed riser anchor base 128; a vertical single or bundled riser pipe(s) 136 anchored to the seabed anchor base 128; a buoyancy tank 132 providing an uplift tension to vertical riser pipe(s) 136; a flexible pipe 134 connecting the top of the vertical riser 136 to the surface process facilities (FPSO) 140; and a flexible joint 138 for connecting the buoyancy tank 132 to the vertical riser 136. FPSO 140 is anchored using mooring lines 141, 143, 145 and 147 to suction anchors 142, 144, 146 and 148 respectively.

Accidental flooding of the buoyancy tank 132 could create a potential hazard to the riser system 130 and expose the field to a risk of catastrophic failure if a sufficient uplift tension is not applied to the vertical pipe system 136. In order to mitigate this risk, instrumentation can be installed to monitor possible accidental flooding of the buoyancy tank 132. Additionally, the buoyancy tank 132, can divided into independent compartments (e.g. vertically stacked or longitudinally) to limit the amount of water that could accidentally fill in the tank.

When buoyancy means, such as buoyancy tank 132, are immersed at depth greater than the conventional depth of human intervention (i.e. greater than 100 meters) the use of Remotely Operated Vehicles (ROVs) allows operations around submersed devices, such as sensor deployment and telemetry plugging.

According to some embodiments, a displacement sensor system 150 is anchored to a structural component of the riser pipe network 130. In the example shown, the displacement sensor system 150 is anchored to section of pipe 250 just below tank 132 just above the flexible joint 138. According to some embodiments, internal or external power means (for example batteries) supply power used by the sensor electronics for signal measurement, and for internal telemetry to relay the information to a piloting system. Although the displacement sensor system 150 is shown anchored to a section of pipe 250 below the buoyancy tank 132 in FIG. 1, according to some embodiments the displacement sensor system is anchored to one or more other elements of the subsea structures shown in FIG. 1. Examples include: measuring strain and/or other types of forces such as hoop or torsion strain of a pipe, such as pipe 124, riser 136 and/or flexible riser pipe 134.

Figure 2:
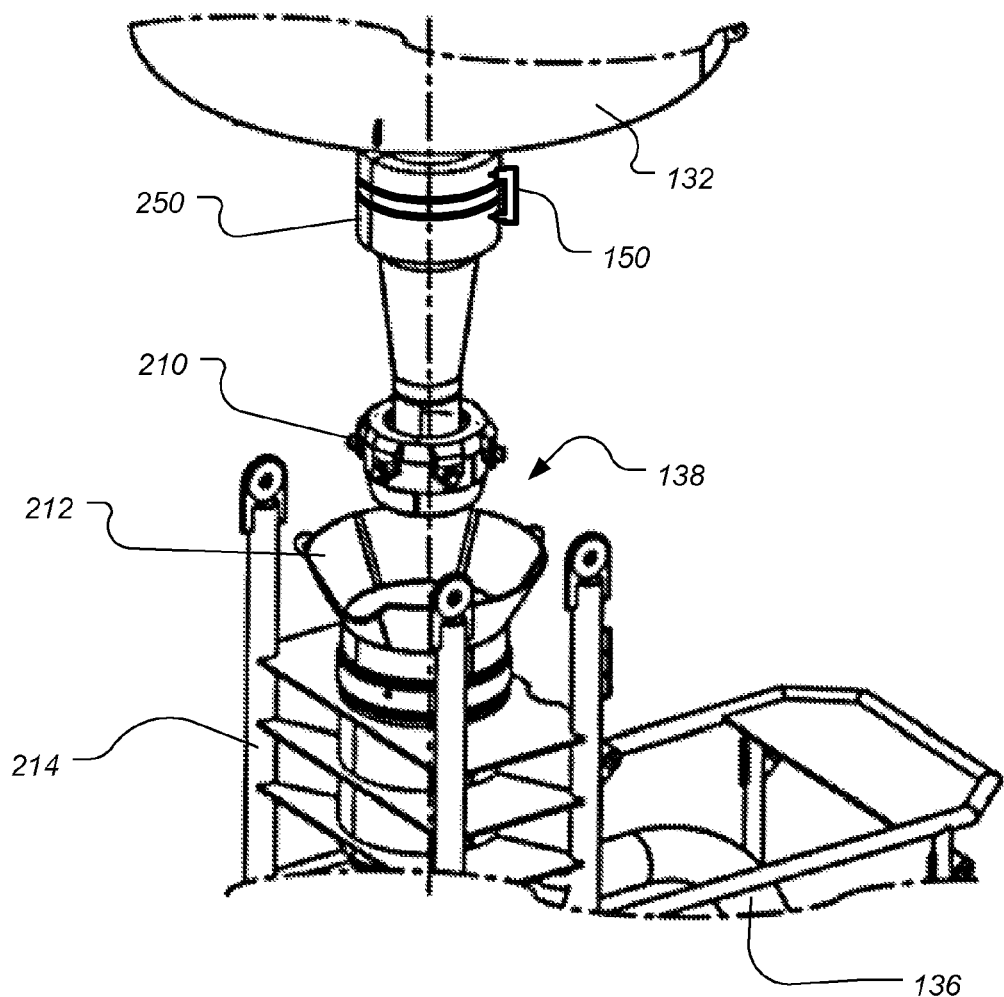
FIG. 2 shows further detail of sensors and a flexible joint between a buoyancy tank, according to some embodiments.

FIG. 2 shows further detail of sensors and a flexible joint between a buoyancy tank, according to some embodiments. Buoyancy tank 132 is flexibly linked to the vertical riser pipe 136 via a flexible joint 138. The flexible joint 138 includes a male connector 210 that mates with a flexible joint receptacle 212 that forms part of an upper riser assembly 214. In the case shown in FIG. 2, the tension generated by the buoyancy tank 132 can be permanently monitored by means of displacement monitoring sensor system 250, which can be configured to measure the pipe strain. Such a system 150 can be useful for monitoring a sudden event as well as for slow water intrusion inside the tank 132, due for instance to corrosion.

In a subsea production system example such as shown in FIGS. 1 and 2, it is preferable that the tension force on the top end of the riser is continuously monitored. Given the system layout, this force can be calculated from the buoyancy force generated by the buoyancy tank 132. However, during its service life, minor water leaks may occur to some of the compartments of the tank 132, which may have a multi-compartmental design. Such leaks may cause accumulation of the water (flood water) in the leaking compartments and gradually change the buoyancy force. Consequently, it is desirable to closely monitor the buoyancy force for such gradual changes in order to avoid serious consequences.

One typical known approach of monitoring the tension force is by installing a conventional strain measurement system on the pipe section 250 that connects the buoyancy tank to the riser. The strain of the connecting section may be measured by a known technique such as a strain gauge, an optical fiber based strain gauge (FBG), or a LVDT transducer. Ideally, the measured strain should be a proportional representation of the tension force. However, it has been found that the stability of such strain sensors and the possible slip of the clamps that couple the sensors to the structure under monitoring can cause errors and long-term drift in the baseline of the measurement system, often in such magnitudes that can mask significant accumulation of flood water in the tank.

According to some embodiments, an improved strain gauge sensor system 150 provides increased stability and accuracy. One feature of the system 150 is its ability to work under flexion (the measured displacement is perpendicular to the blade). When compared to conventional strain sensor, this configuration provides low stiffness, large amplitude and high sensitivity.

According to some embodiments, the described displacement sensor system includes bending an instrumented blade equipped with one or several sensing means. Examples of the sensing means include one or more Wheatstone bridges that are bonded to the blade. The system further comprises anchor means. The anchor means may include at least one penetrating spike or any other device that can firmly lock the sensor extremity to the structure so that any structural deformation of deflexion is directly transmitted to the sensor by bending the instrumented blade. Depending on the interface frame of the sensor with the structural element, this system can be configured to measure properties such as: pulling force, torque, bending moments, strain, elongation, internal pipe pressure, or any load deformation experienced by a structure.

Figure 3:
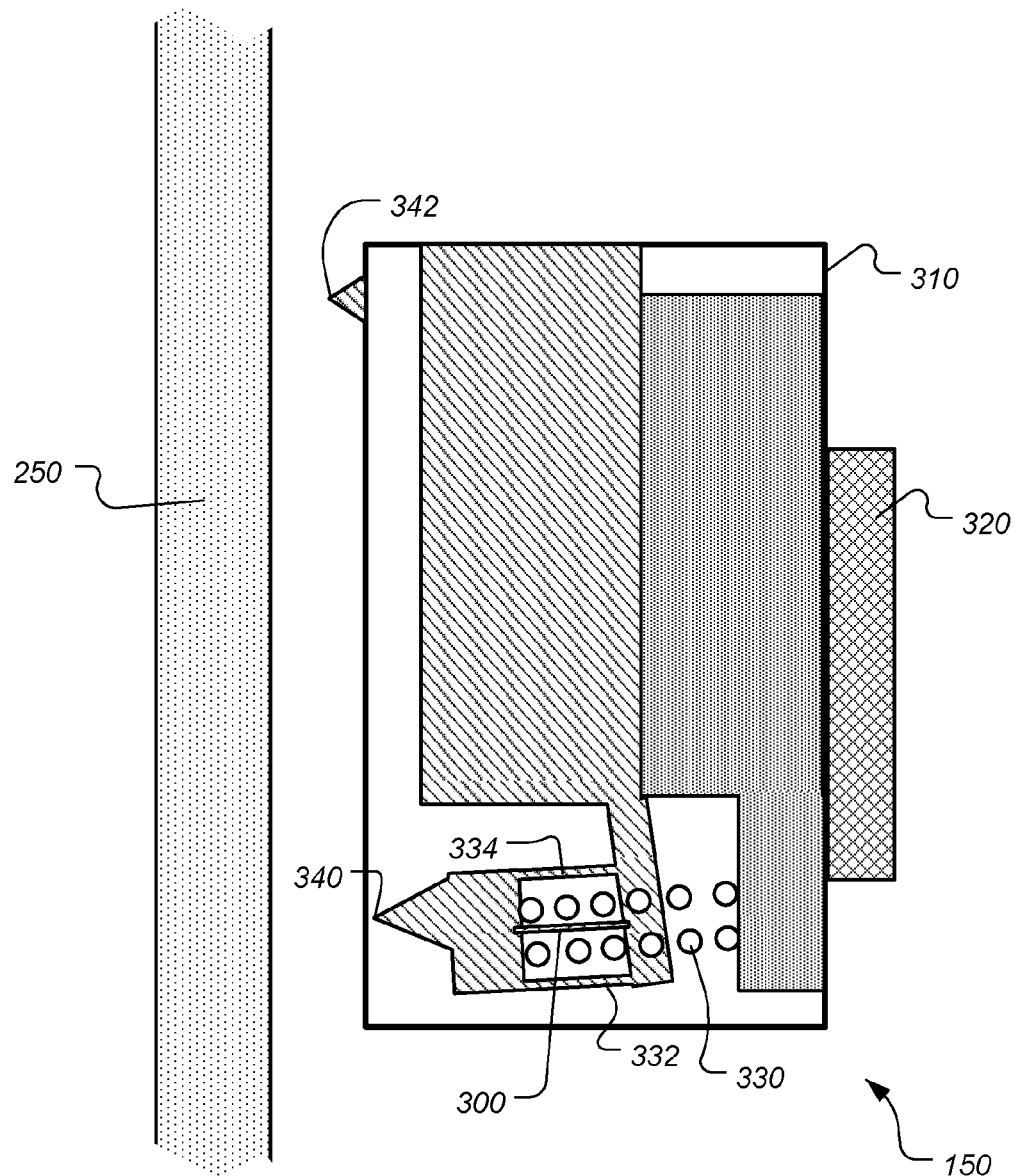
FIGS. 3-5 are block diagrams illustrating aspects of a displacement sensor system, according to some embodiments.
Figure 4:
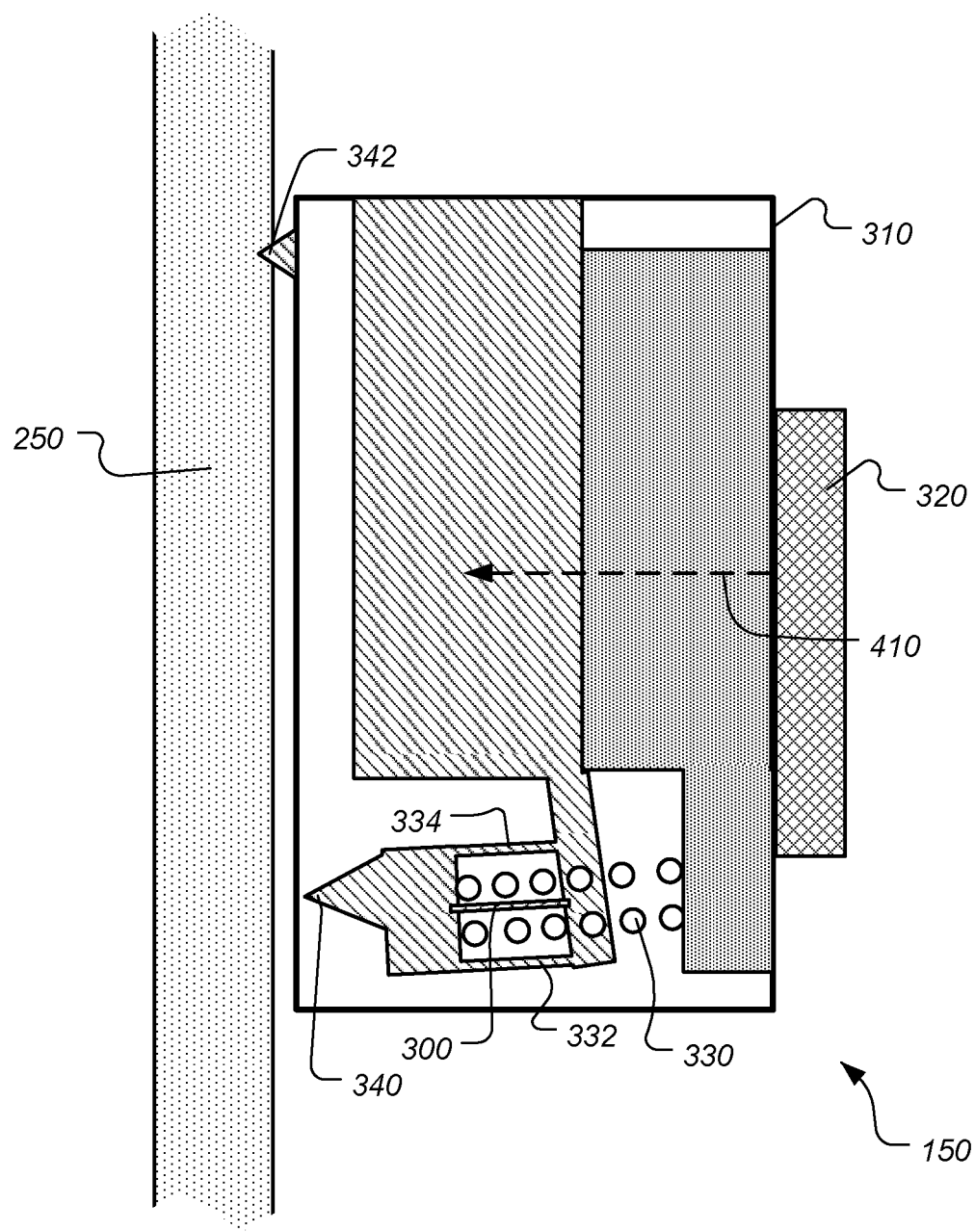
Figure 5:
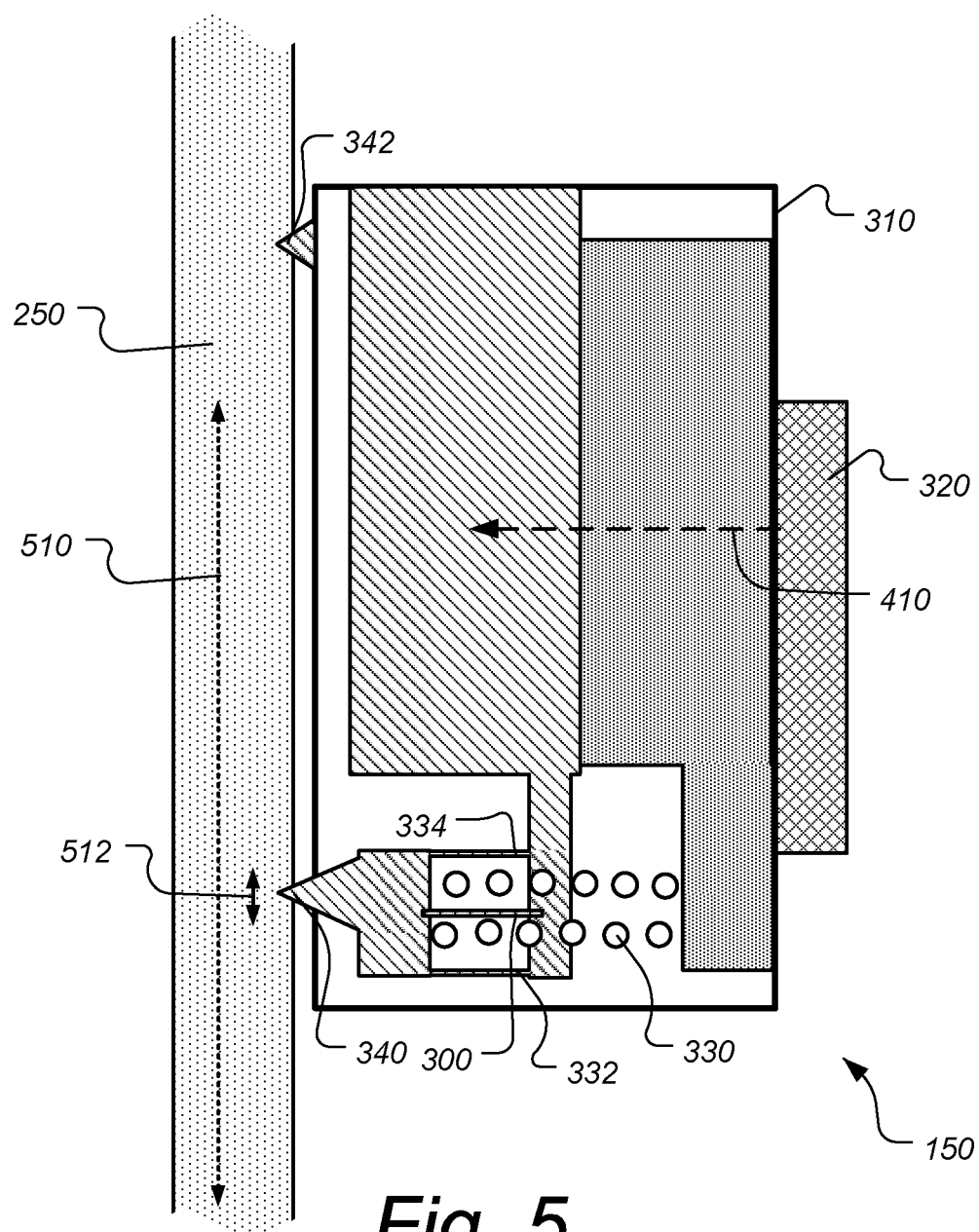

FIGS. 3-5 are block diagrams illustrating aspects of a displacement sensor system, according to some embodiments. FIG. 3 shows a displacement sensor system 150 before installation on a wall 250 of a pipe structure being monitored. The sensor box 310 houses some of the components of the system 150 including a sapphire sensing blade 300, flexible titanium blades 332 and 334 and spring 330. A collar 320 is used to hold the sensor box 310 to the pipe 250. Two anchoring spikes 340 and 342 are also shown (although other numbers of spikes or other anchoring structures can be used). FIG. 4 shows the displacement sensor system upon installation on pipe 250. Note that the upper anchoring spike 342 is firmly engaged with pipe 250 under the force provided by collar 320 (as indicated by dashed arrow 410). The spring 330 in FIGS. 3 and 4 is "loaded" in that it is compressed and is configured to urge the lower anchoring spike 340, sensing blade 300 and flexible titanium blades 332 and 334 towards the pipe 250.

FIG. 5 shows the displacement sensor system after installation on pipe 250. After installation, as shown in FIG. 5, the spring 330 is in a "released" state and lower anchoring spike 340 is firmly engaged on the wall of pipe 250. With both upper and lower anchoring means engaged, as shown in FIG. 5, deformation of the pipe 250 as shown with the dotted arrow 510 will be detected as displacement between the upper and lower anchor positions, as shown by the arrow 512. Note that the distance between these two points 340 and 341 enables to control the sensitivity of the measurement device. For increased sensitivity, this distance should be as large as possible. However, greater distances can also introduce anchoring tolerance issues. In some example applications, a distance between the anchoring points of between about 20 cm and 80 cm has been found to be suitable for a measured displacement between the anchoring points of less than about ten micrometers.

The anchoring point 340 on the displacement sensor 150 is directly connected to at least one bending sensing blade 300 operating within the elastic domain. The blade 300 is configured to work under flexion. Therefore, as represented in FIG. 5, upon installation of the displacement sensor 150 on the structure to be monitored 250, the anchoring point 340 (which in this example is a spike) engages with the structure 250 by releasing spring 330 (which can actually comprise multiple springs). The spring 330 applies a constant load on the termination spike 340 to bite into the structure skin of pipe 250 so that any movement of the structure is directly transmitted to the bending blade 330. An example schematic of this principle is further represented on FIGS. 9A and 9B, infra.

Providing two flexible blades 332 and 334 has been found to avoid bending of the anchoring point itself to minimize drift in the measurement. The instrumented blade 330 can be instrumented with strain resistors (not shown). According to some embodiments, the sensor blade 300 is a high performance sapphire strain blade, mounted in parallel of the two flexible blades 332 and 334.

According to this configuration, the sensor blade 330 being directly coupled to the anchoring point 340 and linked to the monitored structure 250, has been found to provide several advantages: (1) the mechanical transmission chain of the structure skin movement between the anchoring points and the sensing element are substantially reduced; (2) high sensitivity to small displacements can be provided; (3) the installation is independent of the distance between the anchoring points; as a result the sensor module is very compact and might be easily integrated on any interface frame or collar with the structure to monitor; (4) the distance between the upper and lower anchoring points can be maximized; and (5) sensor packaging can be simplified.

Figure 6:
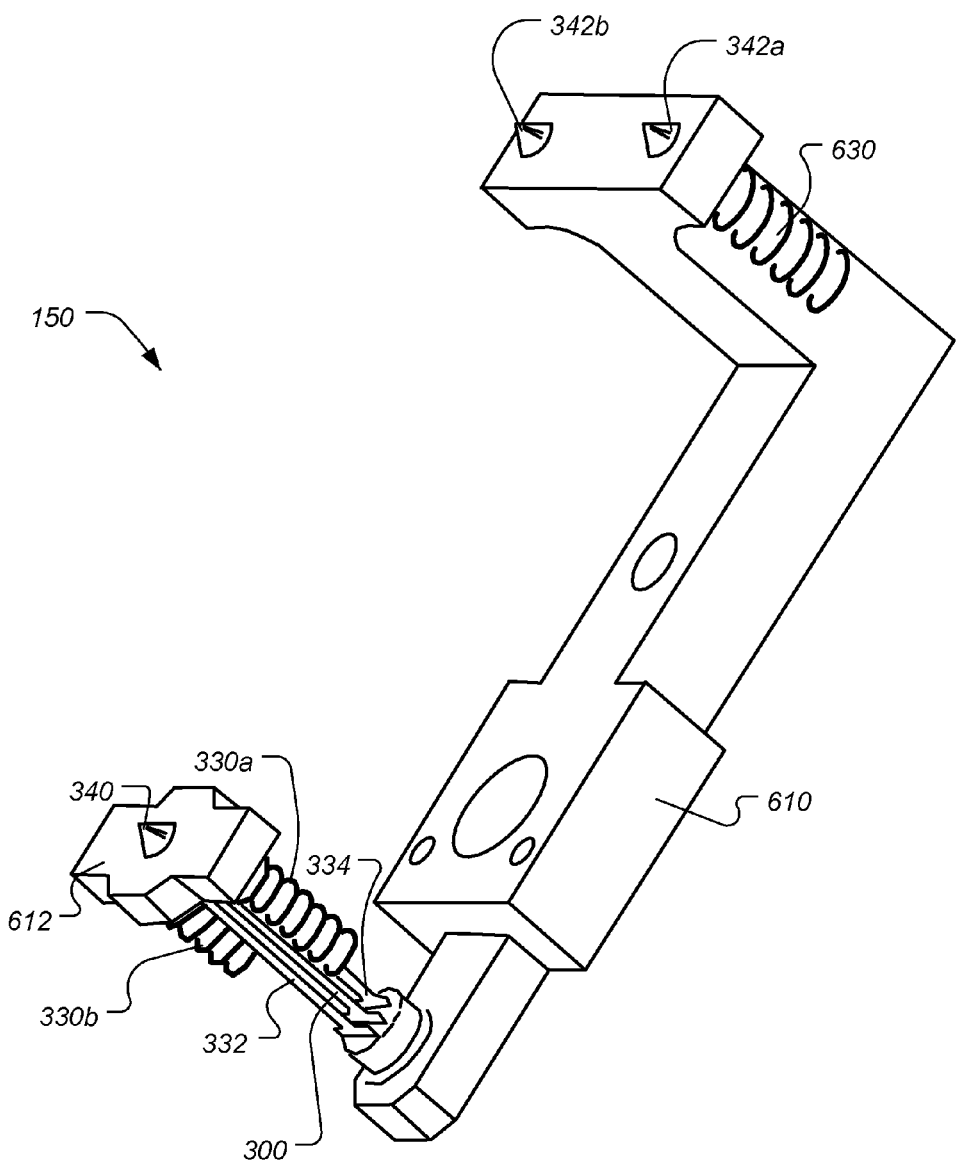
FIG. 6 is a perspective view illustrating aspects of a displacement sensing system, according to some embodiments.

FIG. 6 is a perspective view illustrating aspects of a displacement sensing system, according to some embodiments. In this perspective view of sensing system 150, the upper end of the unit has two anchoring spikes 342a and 342b. According to some embodiments, the two upper anchoring spikes 342a and 342b are spring loaded with springs 630 and 632 respectively. Also visible in FIG. 6 is metal frame 610 to hold the upper and lower ends of the system 150 in rigid alignments. On the lower end of system 150 are two springs 330a and 330b are configured to apply force to lower anchor plate 612 and anchor spike 340 towards the structural element being monitored (not shown).

Figure 7:
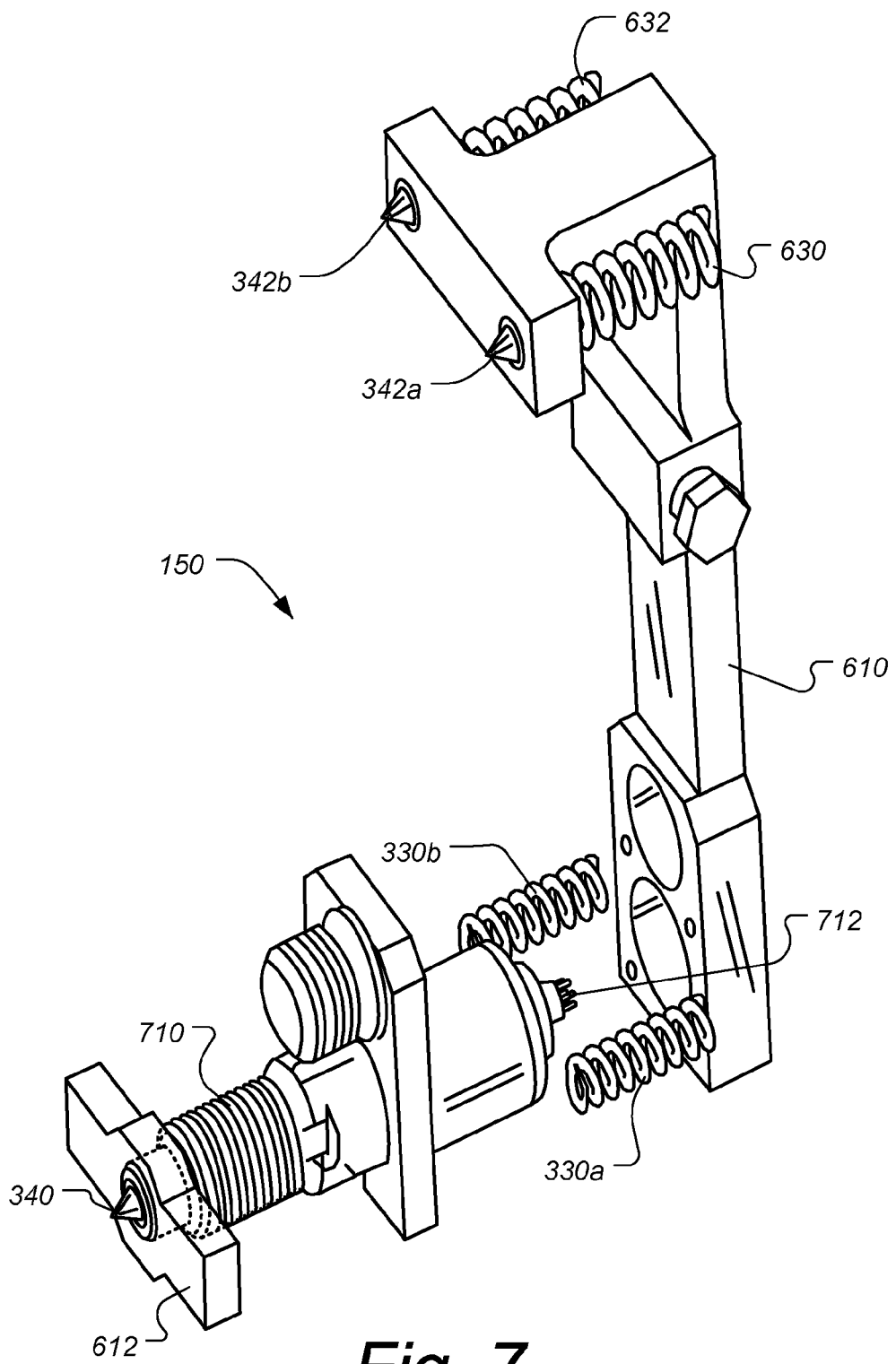
FIG. 7 is a partially exploded perspective view illustrating aspects of a displacement sensing system, according to some embodiments.
Figure 8:
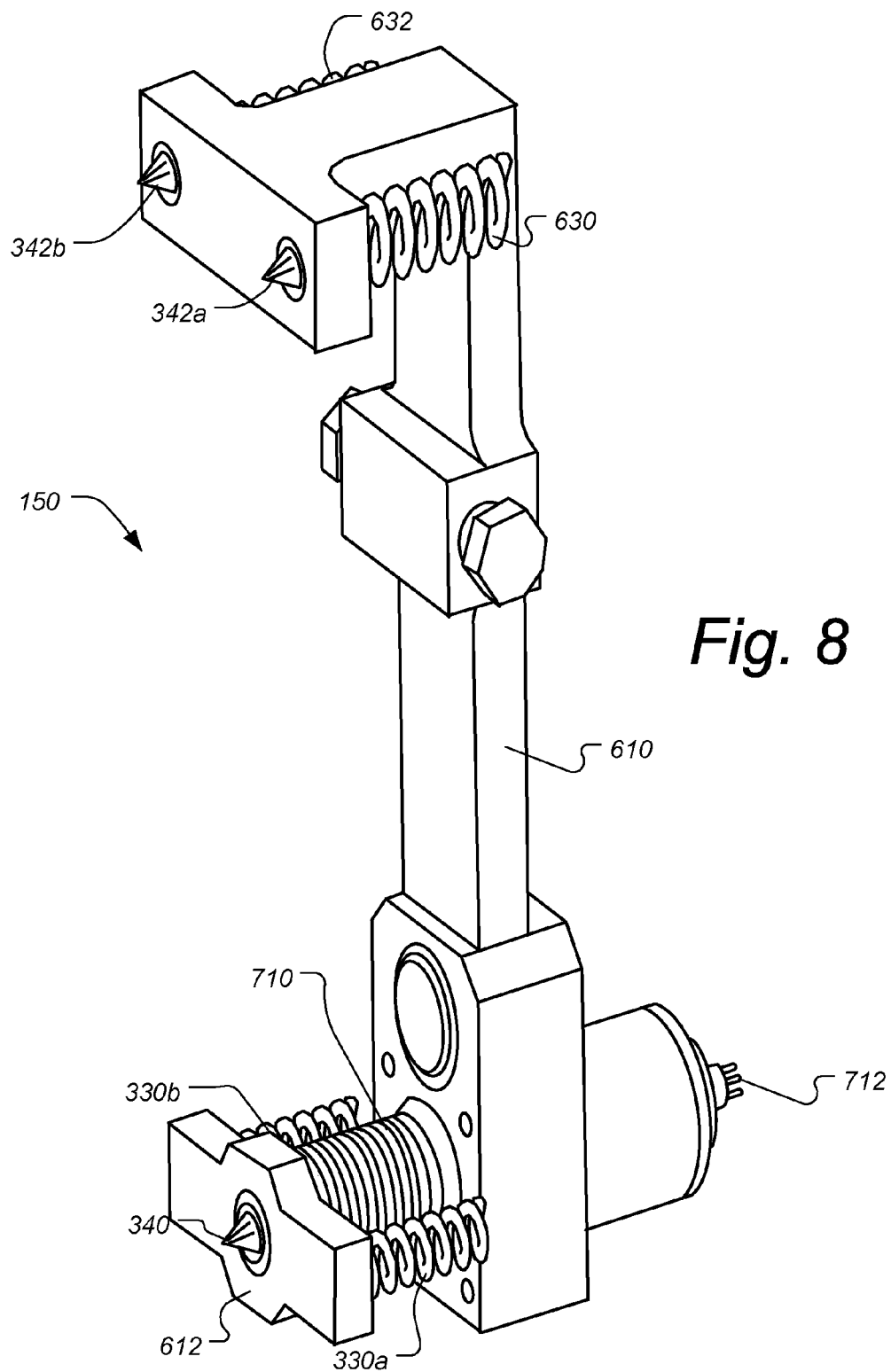
FIG. 8 is a perspective view illustrating aspects of a displacement sensing system, according to some embodiments.

FIG. 7 is a partially exploded perspective view illustrating aspects of a displacement sensing system, according to some embodiments. Visible in FIG. 7 are a bellows 710 that surround the sensing blade and the flexible non-sensing blades. Also visible in FIG. 7 are several electrical connection pins 712 for communication with the electronics of the sensing elements. FIG. 8 is a perspective view illustrating aspects of a displacement sensing system, according to some embodiments. It has been found that configuring the sensing blade 300 in a perpendicular orientation to the direction of displacement being sensed, in combination with the additional non-sensing flexible elements 332 and 334, provides a highly sensitive as well as highly robust displacement sensor system that is well suited to applications such as long-term sub sea monitoring.

Figures 1, 9:
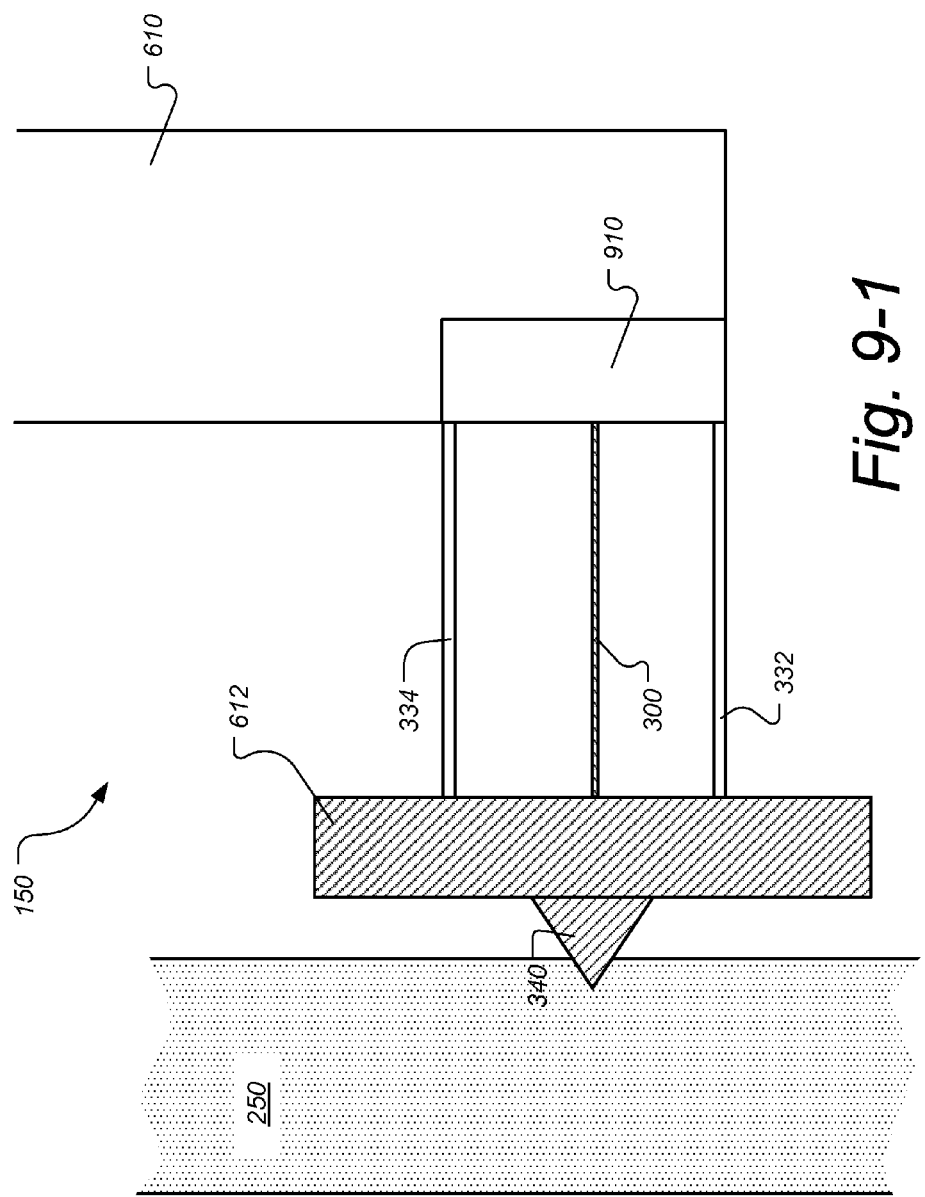
Figures 2, 9:
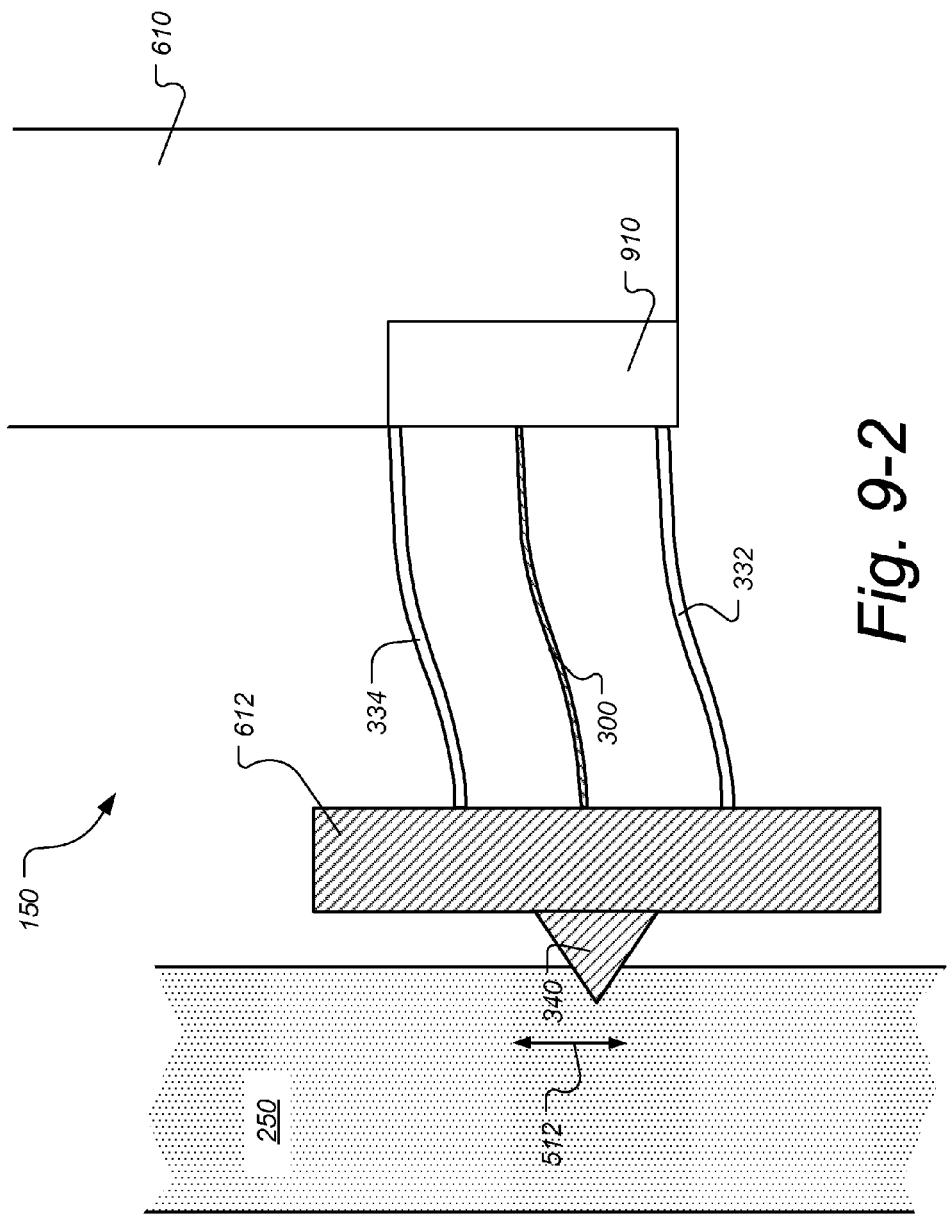

FIGS. 9-1 and 9-2 are diagrams illustrating physical principal aspects of a displacement sensing system, according to some embodiments. Visible are portions of the sensing system 150 with anchoring point 340 engaged with pipe wall 250. In FIG. 9-1 the sensing blade 300 and non-sensing blades 332 and 334 are not significantly being strained. In FIG. 9-2, the anchoring point 340 is displaced downward with respect to frame 610 (and upper anchoring points that are not shown) so as to put strain on sensing blade 300, as well as on non-sensing blades 332 and 334. As can be seen, the flexible non-sensing blades 332 and 334 define a parallelogram and therefore serve to limit movement on lower anchor plate 612 and anchor point 340 to the direction of displacement being sensed as shown by arrow 512.

Figure 10:
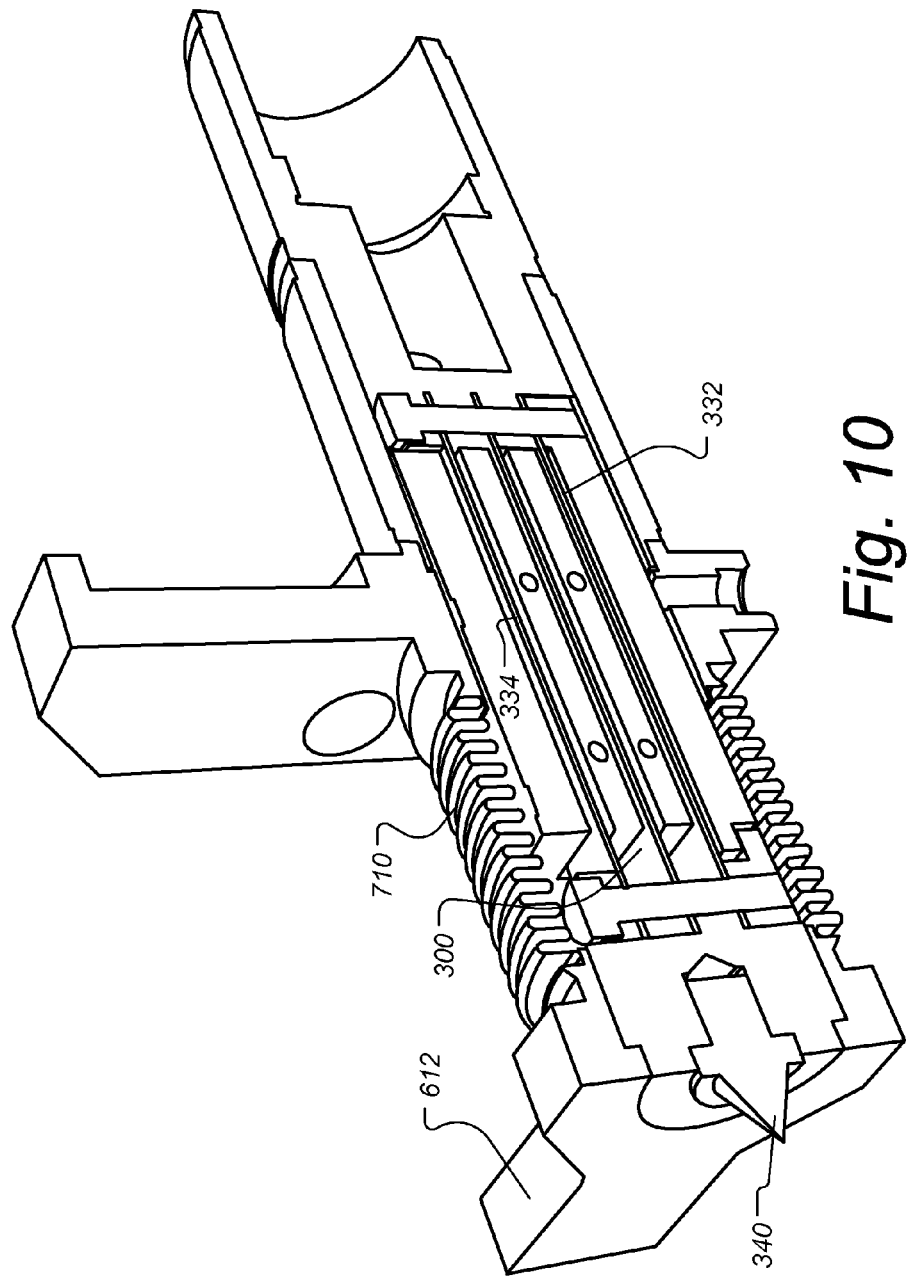
FIG. 10 is a cross section perspective view of aspects of a displacement sensing system, according to some embodiments.

FIG. 10 is a cross section perspective view of aspects of a displacement sensing system, according to some embodiments. Visible is the sensing blade 300 that is rigidly attached at both ends. Specifically, on end is fixed in relation to the frame 610 (not shown), and the other end is fixed in relation to the front plate 612 and anchor point 340. As is visible in FIG. 10, there is no intermediate link between the anchoring point 340 and the sensing blade 330, rather anchoring point 340 and sensing blade 330 are directly linked. Thus, when combined with the dual flexible non-sensing blades 332 and 334, which limit the direction of displacement to direction being sensed, a highly robust yet highly sensitive sensing system is provided, according to some embodiments.

FIG. 11 is a cross section perspective view of aspects of a displacement sensing system using a semi-attached sensing blade, according to some embodiments. In the case of FIG. 11, the sensing blade 300 is only rigidly attached at one end. In particular, the sensing blade 300 is fixed to the rear portion of system, including the frame 610 (not shown). The front end of the sensing blade 300 is held in relation to the frame 610 and anchor point 340 using upper and lower ball bearings 1110 and 1112 as shown.

FIG. 12 is a perspective view illustrating aspects of a sapphire blade for use in displacement sensing, according to some embodiments. The sensing blade 300 is oriented such that its main longitudinal axis is approximately perpendicular to the direction of displacement being sensed (shown by arrow 512). In FIG. 12, blade 300 is shown under strain (with the left side being higher than the right side). It has been found that the locations of greatest strain are areas 1210 and 1212. Thus according to some embodiments the strain gauges are located in areas 1210 and 1212 for greatest sensitivity. According to some embodiments, a crystalline material such as sapphire is used for the main substrate of blade 300. Using sapphire has the advantages of being a good insulator, so that the various resistors (including whetstone bridges), and conducting paths (for example leads 1220) can be easily fabricated directly on the substrate. According to some embodiments the resistors and electrical leads are deposited directly on the sapphire substrate using a plasma sputtering process. Additionally, a crystalline material such as sapphire is very stable and has a relatively low coefficient of thermal expansion. According to some embodiments a resistor-based temperature sensor is also deposited on blade 300 to that thermal effects can be compensated for.

According to some embodiments, the sensor system 150 is integrated with an interface frame other than frame 610 (shown in FIGS. 6, 7 and 8), so that the so-assembled system is configured to measure other types of forces such as hoop or torsion strain of a pipe, such as pipe 124, riser 136 and/or flexible riser pipe 134 shown in FIG. 1. According to some embodiments, the displacement sensor is also independently calibrated and/or tested before being installed on any support frame. According to some embodiments, the sensing blade 300 is made of a non-crystalline material such as titanium, which exhibits good mechanical properties, including good elasticity, low creep, and low hysteresis, as well as having low density. According to other embodiments many other materials could also be used (e.g. Inox 316 L, and Inconel®).

While the present invention has been described in connection with a number of embodiments, and implementations, the present invention is not so limited, but rather covers various modifications, and equivalent arrangements, which fall within the purview of the appended claims.

What is claimed is:

1. A system for sensing displacement on a subsea structural system, the system comprising:
   an elongated frame having a first end and a second end;
   a first anchoring spike mounted to the first end of said elongated frame and configured to anchor said sensing system to a structural element of the subsea structural system at a first location;
   a second anchoring spike configured to anchor said sensing system to the structural element at a second location;
   and a sensing blade with a longitudinal axis, first and second ends, and at least one sensor instrument formed thereon configured to sense bending of said sensing blade, said sensing blade being mounted and configured such that displacement between said first and second locations can be sensed as bending of the sensing blade;
   wherein said longitudinal axis of the sensing blade is non-parallel to a direction of sensed displacement.

2. A system according to claim 1, wherein the sensing blade element has a crystalline material substrate.

3. A system according to claim 2, wherein the crystalline material substrate is sapphire.

4. A system according to claim 1, wherein the longitudinal axis of the sensing blade element is approximately perpendicular to the direction of sensed displacement.

5. A system according to claim 4, wherein two elongated supporting flexible blades have longitudinal axes parallel to said longitudinal axis of said sensing blade and are mounted and configured such that movement of the second anchoring spike is limited to directions parallel to the direction of sensed displacement.

6. A system according to claim 1, wherein the at least one sensor instrument comprises a strain gauge.

7. A system according to claim 6, wherein the at least one sensor instrument comprises two independent strain bridge resistors formed on said sensing blade.

8. A system according to claim 7, wherein said bridge resistors are configured to operate in opposite modes.

9. A system according to claim 1, wherein said sensing blade is further configured and mounted such that displacement between said first and second locations is directly transmitted to bending of said sensing blade.

10. A system according to claim 1, wherein each of the first and second anchoring spikes comprise one or more spikes configured to penetrate the structural element upon installation of the system on said structural element.

11. A system according to claim 1, further comprising at least one elongated supporting flexible member having a longitudinal axis in parallel with said longitudinal axis of said sensing blade.

12. A system according to claim 1, wherein the subsea structural system is a subsea riser system configured to lift a production fluid from a subsurface wellhead to a surface facility.

13. A system according to claim 12, wherein the subsea riser system includes a buoyancy tank configured to provide uplift tension on components of the subsea riser system, and said subsea structural element is under tension due to said uplift tension.

14. A system according to claim 1, wherein said first end of the sensing blade is fixed in rigid relationship with said second end of said elongated frame, and said second end of the sensing blade is fixed in rigid relationship with said second anchoring spike.

15. A system according to claim 1, wherein said first end of the sensing blade is fixed in rigid relationship with either one of the second end of said elongated frame or said second anchoring system, and said second end of the sensing blade is movably attached to other of said second end of said elongated frame or said second anchoring spike.

16. A system according to claim 15, wherein said second end of the sensing blade is contacted by two rounded bearing surfaces so as to be directly influenced by displacement between the first and second anchoring locations.

17. A method of sensing displacement on a subsea structural system, the method comprising:
   sensing bending of an elongated sensing blade having a longitudinal axis and at least one sensor instrument configured to sense bending of said sensing blade; and
   sensing displacement in a sensed displacement direction between first and second locations on a structural element of the subsea structural system, said displacement sensing being based on said sensed bending of said elongated sensing blade, wherein said sensing blade is configured and mounted such that said longitudinal axis is non-parallel to said sensed displacement direction, and such that displacement between said first and second locations is directly transmitted to bending of said sensing blade.

18. A method according to claim 17, wherein said sensing blade is further configured and mounted such that said longitudinal axis is approximately perpendicular to said sensed displacement direction.

19. A method according to claim 17, wherein the subsea structural system is a subsea riser system configured to lift a production fluid from a subsurface wellhead to a surface facility.

20. A method according to claim 19, wherein the subsea riser system includes an uplift system configured to provide uplift tension on components of the subsea riser system, and said structural element is under tension due to said uplift tension and said sensing of displacement is used to monitor the integrity of said uplift system.

21. A method according to claim 20, wherein the uplift system comprises a buoyancy tank configured to provide upward buoyancy force thereby exerting said uplift tension.

22. A method according to claim 17, wherein the at least one sensor instrument comprises a strain gauge.

23. A method according to claim 22, wherein the at least one sensor instrument comprises two independent strain bridge resistors.

24. A method according to claim 17, wherein said elongated sensing blade comprises a crystalline substrate.

25. A method according to claim 24, wherein said crystalline substrate is a sapphire substrate.

26. A method according to claim 17, wherein said elongated sensing blade element comprises a metallic substrate.

27. A method according to claim 17, further comprising automatically transmitting an alert signal to a surface facility when a predetermined threshold value relating to said structural element is met.

28. A method according to claim 17, further comprising determining, based on said sensed displacement, one or more properties associated with the structural element selected from a group consisting of: force; tension; strain and torque.

29. A method according to claim 17, wherein said structural element is a fluid carrying pipe, and said method further comprises estimating fluid pressure within the pipe based on said sensed displacement.

30. A method according to claim 17, further comprising estimating structural fatigue associated with the structural element based on the said sensed displacement.

31. A method according to claim 17, further comprising installing a sensing system including the sensing element on said structural element using an ROV unit.

* * * * *